| United States Patent [19] | [11] Patent Number: 4,871,533 |
| Lagatore | [45] Date of Patent: Oct. 3, 1989 |

[54] COMPOSITION FOR STRENGTHENING FINGERNAILS

[76] Inventor: Tammy Lagatore, 1400 Maple St., Columbia, S.C. 29205

[21] Appl. No.: 75,637

[22] Filed: Jul. 20, 1987

[51] Int. Cl.$^4$ .......................... A61K 7/04; A61K 33/15
[52] U.S. Cl. ........................................ 424/61; 424/670
[58] Field of Search .................................. 424/61, 150

[56] References Cited

U.S. PATENT DOCUMENTS 3,989,817  11/1976  Mayer ..................................... 424/61
4,604,283   8/1986  Gresham ........................... 424/150 X Primary Examiner—Ellis P. Robinson
Assistant Examiner—Susan S. Rucker
Attorney, Agent, or Firm—Bailey & Hardaway

[57] ABSTRACT

A composition and method of producing same is disclosed herein which, when said composition is applied to human fingernails, will cause the fingernails of the user to become harder and stronger. The composition comprises potassium iodide placed into solution with other ingredients which may include ethyl alcohol and distilled water, with the resulting solution applied directly to fingernails as disclosed herein.

9 Claims, No Drawings

COMPOSITION FOR STRENGTHENING FINGERNAILS

BACKGROUND AND SUMMARY OF THE INVENTION

This invention relates to a composition which may be applied directly to human fingernails to strengthen the fingernails and prevent the fingernails from breaking.

It is highly desirable among a large segment of the population to have fingernails which are aesthetically pleasing. These persons desire that their fingernails grow well beyond the tips of the fingers. Since the hands and the digits of most individuals are active, fingernails are particularly subject to breaking and cracking, meaning that they must be cut or trimmed back upon such breaking, precluding growth to the desired point.

To achieve long fingernail growth, or the appearance thereof, various compositions and devices have entered into the market place. These compositions include materials which can be put over the fingernails to effectively increase the thickness and resilience of the fingernail to retard tearing and breaking of the fingernails. Artificial fingernails of the desired shape and length are attached to the person's natural fingernails, so as to produce the appearance of having long fingernails.

The present invention is a composition which is applied directly to the human fingernail and which strengths the fingernail so as to allow it to grow without breaking or tearing. The composition is topically applied periodically to the fingernail, but is not a coating which gives an unnatural appearance, or which is subject to stripping or tearing away from the nail. The present invention actually strengthens the fingernail itself, without leaving a coating upon the nail.

DETAIL DESCRIPTION OF THE PREFERRED EMBODIMENT

The present invention incorporates potassium iodide placed into solution with a carrier which allows the potassium iodide to be applied directly to the human fingernails.

To prepare the composition, which in the preferred embodiment is a solution, a quantity a liquid is heated so as to facilitate the dissolution of the potassium iodide. In the preferred embodiment, this liquid is ethyl alcohol which is heated to approximately one hundred (100) degrees Fahrenheit (38 C.). Potassium iodide is placed into the ethyl alcohol, and is stirred or mixed until the potassium iodide completely dissolves into the ethyl alcohol. It has been found that, by manually stirring, it takes approximately twenty to thirty minutes for the potassium iodide to completely dissolve into the ethyl alcohol.

After the potassium iodide is completely dissolved into the ethyl alcohol, and while the mixture is still warm, distilled water is added. After the distilled water is added, the mixture continues to be heated in the same manner for approximately five to ten minutes.

In the preferred embodiment, the potassium iodide is placed into a carrier solution of ethyl alcohol and water as described above. The carrier solution could be any inert ingredient which is capable of placing the potassium iodide into solution and holding the potassium iodide in solution at room temperature, and which is non-toxic to humans when applied topically to human fingernails. The use of ethyl alcohol and water produces a composition which dries upon application to the fingernail at a desirable rate.

In the preferred embodiment, the potassium iodide comprises about two percent (2%) by volume of the total solution, while the carrier comprises about ninety eight percent (98%) by volume of the total mixture. In the preferred embodiment, this carrier solution of inert ingredients is ethyl alcohol and distilled water of approximately equal proportions.

After the composition is prepared in bulk, it may be placed into smaller containers for use. The composition may be applied by a brush or similar means directly to the fingernail. The composition may be effectively placed on the fingernail even if the fingernail has previously been covered with fingernail polish or a similar coating. It is recommended that the composition be applied three to four times per day for ten to fourteen days, with the number of applications reduced to one to two times per day thereafter. Application may be varied according to the rate of growth of the nails of the individual user, and other similar factors such as the inherent hardness of the user's nails. Once the strengthening of the fingernail has been accomplished, occasional interruption of daily application will not adversely affect the hardness of the nail.

This composition will strengthen the fingernail so as to retard the cracking and breaking of fingernails. The resultant fingernail is harder and less subject to tearing or breaking, allowing the fingernail to grow past the end of the fingertip to the length desired by the user.

What is claimed is:

1. A solution for strengthening nails, consisting essentially of:
   (a) about 9% by weight of potassium iodide; and
   (b) about 91% by weight of one or more inert ingredients suitable for placing said potassium iodide in solution.

2. A solution for strengthening nails, consisting essentially of:
   (a) about 9% by weight of potassium iodide;
   (b) about 50% by weight of ethyl alcohol; and
   (c) about 41% by weight of one or more inert ingredients which may be placed into solution with said potassium iodide and ethyl alcohol.

3. A solution for strengthening nails as described in claim 1, wherein one of said inert ingredients of is distilled water.

4. A solution for strengthening nails as described in claim 2, wherein one of said inert ingredients is distilled water.

5. A process for producing a solution for strengthening nails, consisting essentially of the steps of:
   (a) warming a volume of ethyl alcohol to approximately thirty eight (38) degrees Centigrade;
   (b) adding potassium iodide to said ethyl alcohol in a proportion of about 1 part potassium iodide by weight to 10 parts ethyl alcohol by weight, and creating a solution by mixing said potassium iodide and ethyl alcohol until said potassium iodide is completely dissolved into said ethyl alcohol; and
   (c) adding one or more inert ingredients to said solution of ethyl alcohol and potassium iodide in approximately equal proportions by volume of inert ingredients to said solution and mixing said solution of ethyl alcohol and potassium iodide with said inert ingredients.

6. A process as described in claim 5 wherein one or all of said inert ingredients is distilled water.

7. A solution for strengthening nails produced by the process described in claim 5.

8. A solution for strengthening nails produced by the process described in claim 6.

9. A solution for strengthening nails produced by the process described in claim 5 wherein one or all of said inert ingredients is ethyl alcohol.

* * * * *